United States Patent
Carreira et al.

(10) Patent No.: US 11,981,651 B2
(45) Date of Patent: May 14, 2024

(54) CONVERSION OF THC, CBD AND THEIR DERIVATIVES TO CANNABINOL

(71) Applicants: Swiss CannaPharmaceutical SA, Ecublens (CH); ETH Zürich, Zurich (CH)

(72) Inventors: Erick M. Carreira, Zurich (CH); Roman Sarott, Zurich (CH); Patrick Pfaff, Zurich (CH); Konrad Hurni, St-Sulpice (CH); Remo Roth, Gipf-Oberfrick (CH); Sarah Eichenberger, Wallisellen (CH); Jürg Stäubli, Prangins (CH)

(73) Assignees: SWISS CANNAPHARMACEUTICAL SA, Ecublens (CH); ETH ZURICH, Zurich (CH)

( * ) Notice: Subject to any disclaimer, the term of this patent is extended or adjusted under 35 U.S.C. 154(b) by 25 days.

(21) Appl. No.: 17/839,998

(22) Filed: Jun. 14, 2022

(65) Prior Publication Data
US 2023/0002341 A1  Jan. 5, 2023

(30) Foreign Application Priority Data
Jun. 14, 2021 (EP) .................................... 21179306

(51) Int. Cl.
*C07D 311/80* (2006.01)

(52) U.S. Cl.
CPC ........ *C07D 311/80* (2013.01); *C07B 2200/07* (2013.01)

(58) Field of Classification Search
CPC .................................................... C07D 311/80
See application file for complete search history.

(56) References Cited

PUBLICATIONS

Adams et al., "Structure of Cannabidiol XII. Isomerization to Tetrahydrocannabinols," Isomerization of Cannabidiol of Tetrahydrocannabinols, Aug. 1941, pp. 2209-2213, XP-002208081.
Marzullo et al., "Cannabidiol as the Substrate in Acid-Catalyzed Intramolecular Cyclization," Journal of Natural Products, vol. 83, Sep. 29, 2020, pp. 2894-2901.
Pollastro et al., "Iodine-Promoted Aromatization of p-Menthane-Type Phytocannabinoids," Journal of Natural Products, vol. 81, Dec. 14, 2017, pp. 630-633.

*Primary Examiner* — Sikarl A Witherspoon
(74) *Attorney, Agent, or Firm* — Birch, Stewart, Kolasch & Birch, LLP

(57) ABSTRACT

In a method for aromatizing an alicyclic region of a cannabinoid, especially in enantiopure, scalemic and/or racemic form, in particular for aromatizing the cyclohexene group in $\Delta^9$-THC-$C_5$, $\Delta^9$-THCA-$C_5$ A, $\Delta^9$-THCV-$C_3$, $\Delta^9$-THCVA-$C_5$ A, and/or scalemic or racemic mixtures of these substances, wherein an oxidizing agent is added to the cannabinoid, sulfur is used as the oxidizing agent.

14 Claims, No Drawings

CONVERSION OF THC, CBD AND THEIR DERIVATIVES TO CANNABINOL

TECHNICAL FIELD

The invention relates to a method for aromatizing an alicyclic group of a cannabinoid, especially in enantiopure, scalemic and/or racemic form, in particular for aromatizing the cyclohexene group in $\Delta^9$-THC-$C_5$, $\Delta^9$-THCA-$C_5$ A, $\Delta^9$-THCV-$C_3$, $\Delta^9$-THCVA-$C_5$ A and/or scalemic or racemic mixtures of these substances, wherein an oxidizing agent is added to the cannabinoid. Further, the invention relates to a method for the conversion of a cannabidiol, in particular CBD-$C_5$ and/or CBD-$C_3$, and/or a cannabidiol acid, in particular CBDA-$C_5$ and/or CBDA-$C_3$, to a cannabinol and/or a cannabinolic acid. Another aspect of the present invention is related to the use of an oxidizing agent for aromatizing an alicyclic region of a cannabinoid.

BACKGROUND ART

It is well known, that various p-menthane-type phytocannabinoids and their carboxylated precursors can be converted to Cannabinol by treating with iodine (Pollastro et. al; Journal of Natural Products; 2018, 81, 630-633).

However, the process according to the state of the art has the disadvantage that the yield is relatively low. In addition, the process is expensive.

SUMMARY OF THE INVENTION

It is the object of the invention to provide an improved method for aromatizing cannabinoids, especially Tetrahydrocannabinol (THC), Canabidiol (CBD) and/or their derivatives. Preferably, the cannabinoids should be converted to cannabinols or CBN, respectively. Especially, the method should give an increased yield. Furthermore, the method should be feasible with substances that are as non-toxic as possible and cost-effective.

The solution of the invention is specified by the features of claim 1. Thus, the core of the invention is a method for aromatizing an alicyclic region of a cannabinoid, in particular for aromatizing the cyclohexene group in $\Delta^9$-THC-$C_5$, $L^9$-THCA-$C_5$ A, $L^9$-THCV-$C_3$ and/or $L^9$-THCVA-$C_5$ A, wherein an oxidizing agent is added to the cannabinoid. Thereby sulfur is used as the oxidizing agent. In particular, the cannabinoid, especially $\Delta^9$-THC-$C_5$, $\Delta^9$-THCA-$C_5$ A, $\Delta^9$-THCV-$C_3$ and/or $\Delta^9$-THCVA-$C_5$A, can be present in enantiopure, scalemic and/or racemic form. Regarding sulfur, any sulfur allotrope of mixtures of two or more sulfur allotropes can be used.

Experiments showed surprisingly that the use of sulfur as oxidizing agent leads to a better yield when compared with other oxidizing agents. Also, the inventive method is scalable without negatively affecting the yield. Finally, the use of sulfur leads to an inexpensive process for the conversion of cannabinoids such as Tetrahydrocannabinol (THC), Canabidiol (CBD) and/or their derivatives to CBN.

Further, the use of sulfur has—in comparison to iodine for example—the advantage that it is less toxic. This is of particular advantage if the resulting CBN is used for medical or therapeutic purposes. Thus, a purifying process of the CBN can be less costly. Depending on the application of the CBN, a purifying process can also be dispensed with, if the amount of sulfur in the CBN does not affect the use of the CBN.

In particular, the cannabinoid is meant to be a phytocannabinoid. These kind of substances are for example found in *cannabis*.

An alicyclic region comprises one or more all-carbon rings which may be either saturated or unsaturated. Alicyclic rings are not aromatic. The alicyclic region of the cannabinoid is preferably a cyclohexene region. However, the alicyclic region could also be a cyclohexadiene. The cyclohexene group exists in particular in cannabinoids, for example in $\Delta^9$-THC-$C_5$, $L^9$-THCA-$C_5$ A, $L^9$-THCV-$C_3$ as well as in $\Delta^9$-THCVA-$C_3$ A.

$\Delta^9$-THC-05 is also known as $\Delta^9$-tetrahydrocannabinol. $\Delta^9$-THCA-$C_5$ A is also known as Delta-9-tetrahydrocannabinolic acid. It differs from $\Delta^9$-THC-$C_5$ by a carboxylic acid group. $\Delta^9$-THCV-$C_3$ is also known as Tetrahydrocannabivarin and $\Delta^9$-THCVA-$C_3$ A is also known as Tetrahydrocannabivarinic acid. The structures and other chemical or physical data of these compounds are well known by the skilled in the art. Preferably the compounds above are intermediate products, which are converted to CBN and its derivatives as follows.

Preferably the cannabinoid is converted to a cannabinol, in particular to CBN-$C_5$ and/or CBN-$C_3$. Therewith, the converted product can for example be used as a therapeutic to ease symptoms and side effects of neurological conditions, including epilepsy, seizures, and uncontrollable muscle stiffness. Further, CBN is believed to be effectively as a sleep aid or sedative and could also be used in corresponding therapies. There are lots of other fields of application for CBN. However, with the inventive process, the cannabinoid can in principle be converted to other chemical compounds known by the person skilled in the art.

Preferably cyclooctasulfur is used as oxidizing agent. Cyclooctasulfur is preferred because it is inexpensive and easy to dose. However, in principle any sulfur allotrope or mixtures of two or more sulfur allotropes can be used as the oxidizing agent as well.

In the following, the term "equivalent" is understood to mean a molar equivalent, i.e. 1 equivalent is proportional to 1 mol of the substance.

Preferably between 1.5 and 2.5, preferably 2, equivalents of sulfur are added to one equivalent of cannabinoid. 2 equivalents of sulfur are in particular used for aromatizing of a cyclohexen group, where two additional double-bonds have to be formed in order to aromatize the alicyclic region of the cannabinoid. However, the equivalent could also be less, if for example a cyclohexadien has to be aromatized or the equivalent could be more, if either several alicyclic groups have to be aromatized or a cyclohexane group has to be aromatize. If a short reaction time is of high priority, more than 2 equivalents of sulfur can be added to one equivalent of cannabinoid.

Preferably the cannabinoid is heated with the sulfur, in particular to a temperature between 150° C. and 350° C., preferably to a temperature between 200° C. and 300° C., in particular to a temperature between 240° C. and 260° C. Experiments have shown that in the preferred temperature region, the best yield could be achieved. While at lower temperature, the yield is less, at higher temperatures the risk of decomposition of the resulting cannabidiol increases. Nonetheless, the temperature can also be below 150° C. wherewith a gentle conversion can be established in particular if thermally instable substances are contained in the matrix which might be intentional in the product.

In a method for the conversion of a cannabidiol, in particular CBD-$C_5$ and/or CBD-$C_3$, and/or a cannabidiol acid, in particular CBDA-$C_5$ and/or CBDA-$C_3$, to a cannabinol and/or a cannabinolic acid, respectively, an acid- or base-promoted cyclization is carried out in a first step and the above described method for aromatizing an alicyclic group of the cannabinol and/or the cannabinolic acid is carried out in a second step. Preferably the cyclization is acid-promoted. However, base-promoted cyclization is also possible. Thereby, preferably, the cannabidiol, is present in enantiopure, scalemic and/or racemic form. Especially the cannabidiol is selected from $CBD-C_5$ and/or $CBD-C_3$ and/or cannabidiol acid, in particular $CBDA-C_5$ and/or $CBDA-C_3$, in enantiopure, scalemic and/or racemic form.

Preferably in the first step cannabidiol and/or the cannabidiolic acid is dissolved in an organic solvent, in particular toluene, and is mixed with an acid, in particular p-toluenesulfonic acid, to achieve the cyclization. It has been shown, that the use of toluene as solvent is ideal because of the low costs wherewith an economic method for the first step can be established. Also, the use of p-toluenesulfonic acid is preferred, since therewith an efficient acid based cyclization can be established by an electrophilic addition to the non-aromatic double bond. However, the person skilled in the art is aware of other solvents than toluene for solving the cannabidiol and/or the cannabidiolic acid and other acids than p-toluenesulfonic acid are known by the skilled person for the cyclization.

Preferably in the first step between 0.05 and 0.15 equivalent of p-toluenesulfonic acid, preferably between 0.09 and 0.11 equivalent of p-toluenesulfonic acid, is added to one equivalent of cannabidiol or cannabidiolic acid, respectively. Most preferably, 0.1 equivalent of p-toluenesulfonic acid is added to one equivalent of cannabidiol or cannabidiolic acid, respectively. Therewith, the yield is maximized by a minimum amount of p-toluenesulfonic acid, wherewith the method can be carried out particularly cost-effectively. However, if 100% conversion or a short reaction time is of high importance, more than 0.15 equivalent of p-toluenesulfonic acid can be added to one equivalent of cannabidiol or cannabidiolic acid, respectively.

In the first step the cannabidiol and/or the cannabidiolic acid dissolved in the organic solvent is heated to a temperature between 80° C. and 250° C., preferably to a temperature between 100° C. and 180° C., in particular to a temperature between 120° C. and 160° C. The higher the reaction temperature, the faster the reaction can be carried out. On the other hand, it should be noted that if the reaction temperature is too high, the reactant or the product may also decompose. Experiments have shown that the preferred temperature range leads to optimum yields with short reaction times.

In a preferred method $CBD-C_5$ is subjected to acid-based cyclization in a first step and is subsequently reacted with sulfur as oxidant to form $CBN-C_5$. $CBN-C_5$ is the most important cannabinol. However, also the mixture of $CBD-C_5$ and $CBD-C_3$ or $CBD-C_3$ can be subjected to acid-based cyclization in the first step. If a mixture of $CBD-C_5$ and $CBD-C_3$ is used as educt, the product can be separated, e.g. by chromatography, to get the $CBN-C_5$ or the $CBN-C_3$ respectively. However, in several cases the mixture does not affect the use in therapeutics and other applications.

In the first step, CBD is dissolved in toluene in a flask equipped with reflux condenser and $pTsOH.H_2O$ is added in one portion. The resulting colorless solution is heated to a temperature between 120° C.-160° C. and stirred at reflux for preferably between 0.5 and 3 h, more preferably for about 1.5 h. The consumption of CBD is preferably observed by TLC (thin layer chromatography), however also other analytic techniques are suitable. For the TLC analysis preferably $CH_2Cl_2$/hexanes (mixed 1:1 per vol.) is used. When the TLC shows full consumption of CBD, the reaction can be stopped.

In a preferred method, the resulting cannabinoid is separated by an extraction method. In particular, for the separations, preferably deionized water is added to the reaction mixture in order to separate the organic layer. The aqueous phase is preferably extracted with EtOAc (ethyl acetate). The combined organic extracts are preferably washed with a saturated aqueous solution of $NaHCO_3$, then water and finally with brine. The product is then preferably dried over $MgSO_4$ and concentrated under reduced pressure.

In other variants of the method, the purifying process, in particular the extraction method explained above can be omitted. It can be sufficient to evaporate or to distil the toluene out of the cannabinoid.

Preferably, in the second step, to the unpurified, reddish oil obtained in the first step sulfur is added and the mixture is heated preferably to a temperature between 200° C. and 300° C., in particular to about 250° C.

In a preferred variant of the method, the unpurified product from the second step is purified by flash column chromatography to obtain CBN as an orange oil. However, the purity of the unpurified product from the second step can be sufficient can be sufficient for several applications. Further also other purification methods (other than flash column chromatography) can be used, for example distillation under reduced pressure or the like.

Another aspect of the present invention is directed to the use of sulfur as an oxidizing agent for aromatizing an alicyclic region of a cannabinoid, in particular for aromatizing the cyclohexene group in $\Delta^9$-THC-$C_5$, $\Delta^9$-THCA-$C_5$ A, $\Delta^9$-THCV-$C_3$ and/or $\Delta^9$-THCVA-$C_3$ A.

Thereby, preferably, the cannabinoid is obtained by acid- or base-promoted cyclization of a cannabidiol, in particular $CBD-C_5$ and/or $CBD-C_3$, and/or a cannabidiol acid, in particular $CBDA-C_5$ and/or $CBDA-C_3$.

Preferred implementations described above with respect to the inventive method are likewise preferred with the inventive use.

Other advantageous embodiments and combinations of features come out from the detailed description below and the entirety of the claims.

PREFERRED EMBODIMENTS

In a first step, CBD (0.010 kg, 0.032 mol, 1.0 equiv) was dissolved in toluene (320 mL) in a 500 mL three-necked round-bottomed flask equipped with reflux condenser and $pTsOH.H_2O$ (0.61 g, 3.2 mmol, 0.1 equiv) was added in one portion. The resulting colorless solution was heated to 140° C. and stirred at reflux for 1.5 h, after which TLC analysis (1:1 $CH_2Cl_2$/hexanes) showed full consumption of CBD. The reaction mixture was cooled to ambient temperature and deionized water (50 mL) was added. After separation of the organic layer, the aqueous phase was extracted with EtOAc (2×120 mL). The combined organic extracts were washed with sat. aq. $NaHCO_3$ (75 mL), water (80 mL) and brine (80 mL), dried over $MgSO_4$ and concentrated under reduced pressure.

In a second step, to the unpurified, reddish oil obtained in step 1 was added sulfur (2.0 g, 8.0 mmol Ss, 0.25 equiv) in a 50 mL round-bottomed flask, and the mixture was heated neat to 250° C. in an aluminium heating block. After separation of the organic layer, the aqueous phase was extracted with EtOAc (2×80 mL). The combined organic extracts were washed with water (80 mL) and brine (80 mL), dried over $MgSO_4$ and concentrated under reduced pressure.

The unpurified product was purified by flash column chromatography ($SiO_2$, eluting in hexanes 2% to 3% EtOAc/hexanes, using a total of 15 L of technical grade solvent) to obtain CBN as an orange oil (7.3 g, 74% yield).

In this preferred embodiment of the inventive method as shown in the following reaction scheme, CBD-$C_5$ is converted in the first step to $\Delta^9$-THC-$C_5$ by an electrophile addition to the double binding resulting in an acid-based cyclisation using p-toulenesulfonic acid. In the second step, $\Delta^9$-THC-$C_5$ is aromatized and converted by sulfur to CBN-$C_5$:

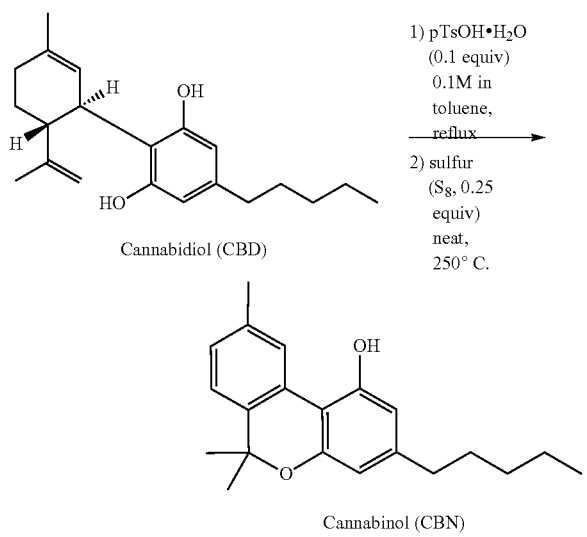

Attempts indicate that purification of crude CBN by vacuum distillation is feasible and could be a preferred method for purification on larger scale (200° C., 0.01 mbar, see Justus Liebigs Annalen der Chemie, 1960, 630, 71-83). However, in several fields of application, the purification is not necessary or can be done more efficiently by methods well known by the skilled in the art.

Further experiments showed the following yields depending on the size of the batch:

TABLE 1

Yield of CBN depending on the batch size

| Amount of CBD | Yield of CBN |
|---|---|
| 500 mg | 67% |
| 1 g | 70% |
| 5 g | 68% |
| 10 g | 74% |

Comparing with the state of the art according to J. Nat. Prod. 2018, 81, 630-630, where a yield of only 60% of a 1 g scale has been achieved, the inventive method is significantly better, as for the 1 g scale of the invention an yield of 70% could be achieved.

In summary, it is to be noted that a method for aromatizing an alicyclic region of a cannabinoid is established, wherewith a particularly high yield can be achieved at low cost.

The invention claimed is:

1. Method for aromatizing an alicyclic region of a cannabinoid, wherein an oxidizing agent is added to the cannabinoid, wherein sulfur is used as the oxidizing agent, wherein the cannabinoid is converted to a cannabinol and the cannabinol is CBN-$_5$ and/or CBN-$C_3$.

2. Method according to claim 1, wherein the cannabinoid is present in enantiopure, scalemic and/or racemic form.

3. Method according to claim 1, wherein the alicyclic region of the cannabinoid is the cyclohexene group in $\Delta^9$-THC-$C_5$, $\Delta^9$-THCA-$C_5$ A, $\Delta^9$-THCV-$C_3$, $\Delta^9$-THCVA-$C_5$ A, and/or scalemic or racemic mixtures of these substances.

4. Method according to claim 1, wherein cyclooctasulfur is used as oxidizing agent.

5. Method according to claim 1, wherein between 1.5 and 2.5 equivalents of sulfur are added to one equivalent of cannabinoid.

6. Method according to claim 1, wherein the cannabinoid is heated with the sulfur to a temperature between 150° C. and 350° C.

7. Method for the conversion of a cannabidiol to a cannabinol and/or a cannabinolic acid, respectively, wherein an acid- or base-promoted cyclization is carried out in a first step and the method according to claim 1 is carried out in a second step.

8. Method according to claim 7, wherein the cannabidiol is CBD-$C_5$ and/or CBD-$C_3$, and/or a cannabidiolic acid and/or scalemic or racemic mixtures of these substances.

9. Method according to claim 8, wherein the cannabidiolic acid is CBDA-$C_5$ and/or CBDA-$C_3$ and/or scalemic or racemic mixtures of these substances.

10. Method according to claim 8, wherein in the first step cannabidiol or the cannabidiolic acid, respectively, is dissolved in an organic solvent and is mixed with an acid to achieve the cyclization.

11. Method according to claim 10, wherein the organic solvent is toluene and/or the acid is p-toluenesulfonic acid.

12. Method according to claim 11, wherein in the first step between 0.05 and 0.15 equivalent of p-toluenesulfonic acid is added to one equivalent of cannabidiol or cannabidiolic acid, respectively.

13. Method according to claim 10, wherein in the first step the cannabidiol and/or the cannabidiolic acid dissolved in the organic solvent is heated to a temperature between 80° C. and 250° C.

14. Method according to claim 8, wherein CBD-$C_5$ is subjected to an acid-based cyclization in a first step and is subsequently reacted with sulfur as oxidant to form CBN-$C_5$.

* * * * *